United States Patent [19]

Nakasima et al.

[11] Patent Number: 5,220,912
[45] Date of Patent: Jun. 22, 1993

[54] LIGHT SOURCE APPARATUS FOR ENDOSCOPE

[75] Inventors: Masaaki Nakasima; Katsuhiko Furuya; Tadashi Takahashi, all of Tokyo, Japan

[73] Assignee: Asahi Kogaku Kogyo Kabushiki Kaisha, Tokyo, Japan

[21] Appl. No.: 598,425

[22] Filed: Oct. 16, 1990

[30] Foreign Application Priority Data

Oct. 17, 1989 [JP] Japan .................. 1-270910

[51] Int. Cl.⁵ .............................. A61B 1/06
[52] U.S. Cl. ............................ 128/6; 128/4
[58] Field of Search ............ 128/6, 4, 11, 23, 397, 128/396, 634, 633, 901; 606/16, 15, 14, 13, 2, 10, 11

[56] References Cited

U.S. PATENT DOCUMENTS

| | | | |
|---|---|---|---|
| 4,224,643 | 1/1981 | Tokutomi | 360/70 |
| 4,557,575 | 12/1985 | Tano et al. | 354/289.1 |
| 4,588,927 | 5/1986 | Kanno et al. | 604/67 X |
| 4,933,843 | 6/1990 | Scheller et al. | 604/22 X |

FOREIGN PATENT DOCUMENTS 0039047 11/1981 European Pat. Off. .
60-34428 2/1985 Japan .

OTHER PUBLICATIONS

H. Feichtinger. *Mikrocomputer Von A Bis Z*. Franzis Elektronik-Nachschlagewerk. 1982. pp. 52-53.

Primary Examiner—John J. Wilson
Assistant Examiner—Jeffrey A. Smith
Attorney, Agent, or Firm—Sandler Greenblum & Bernstein

[57] ABSTRACT

A light source apparatus for an endoscope comprises a light source for supplying light to the endoscope for illuminating an object, a microcomputer for effecting operation control, and an erasable programmable read only memory for storing data that is used in the microcomputer. The read only memory may be replaced with a access memory that has a chip select terminal connected to a programmable input/output interface, which is connected to a system bus of the microcomputer, in such a manner that the random access memory will not be selected when all output ports of the interface are set to either a high or low level.

12 Claims, 4 Drawing Sheets

LIGHT SOURCE APPARATUS FOR ENDOSCOPE

BACKGROUND OF THE INVENTION

1. Field of the Invention

The present invention relates to a light source apparatus for an endoscope, which has a programmable memory for storing data used in endoscopic operations.

2. Description of the Prior Art

Various kinds of data may be used on various occasions in a light source apparatus for an endoscope, for example, on setting conditions for effecting automatic exposure photographing, on setting a brightness level of illuminating light during observation, or on setting letters which are to be superimposed on a picture taken through the endoscope. Such data must be input by an operator (e.g., a doctor). It is however, troublesome to input necessary data on each and every particular occasion.

Accordingly, it is conventional practice to store data that has a high probability of frequent use in a random access memory (RAM), which is connected directly to a system bus in a microcomputer.

In such a light source apparatus, however, an ignition noise is generated when a light source, such as a xenon lamp, is turned on, and it is also likely that external noise from an external device may enter the apparatus.

In conventional arrangements having a RAM connected directly to the system bus, such an internal or external noise may destroy, erase or rewrite the data stored in the RAM, resulting in maloperation when the system is controlled afterward on the basis of the affected data.

SUMMARY OF THE INVENTION

An object of the present invention is to provide a light source apparatus for an endoscope, which is designed so that data stored in a programmable memory will not be destroyed by noise or other disturbances.

Other objects and advantages of the present invention will become apparent from the following detailed description of illustrated embodiments of the invention.

According to the present invention, there is provided a light source apparatus for an endoscope comprising: a light source for supplying light for illuminating an object to the endoscope; a microcomputer for effecting operation control; and an erasable programmable read only memory for storing data that is used in the microcomputer.

In addition, there is provided a light source apparatus for an endoscope comprising: a light source for supplying light for illuminating an object to the endoscope; a microcomputer for effecting operation control; and a random access memory for storing data that is used in the microcomputer. The random access memory has a chip select terminal connected to a programmable input/output interface, which is connected to a system bus of th microcomputer in such a manner that the random access memory will not be selected when all output ports of the interface are set to either a high or low level.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Figure 1:
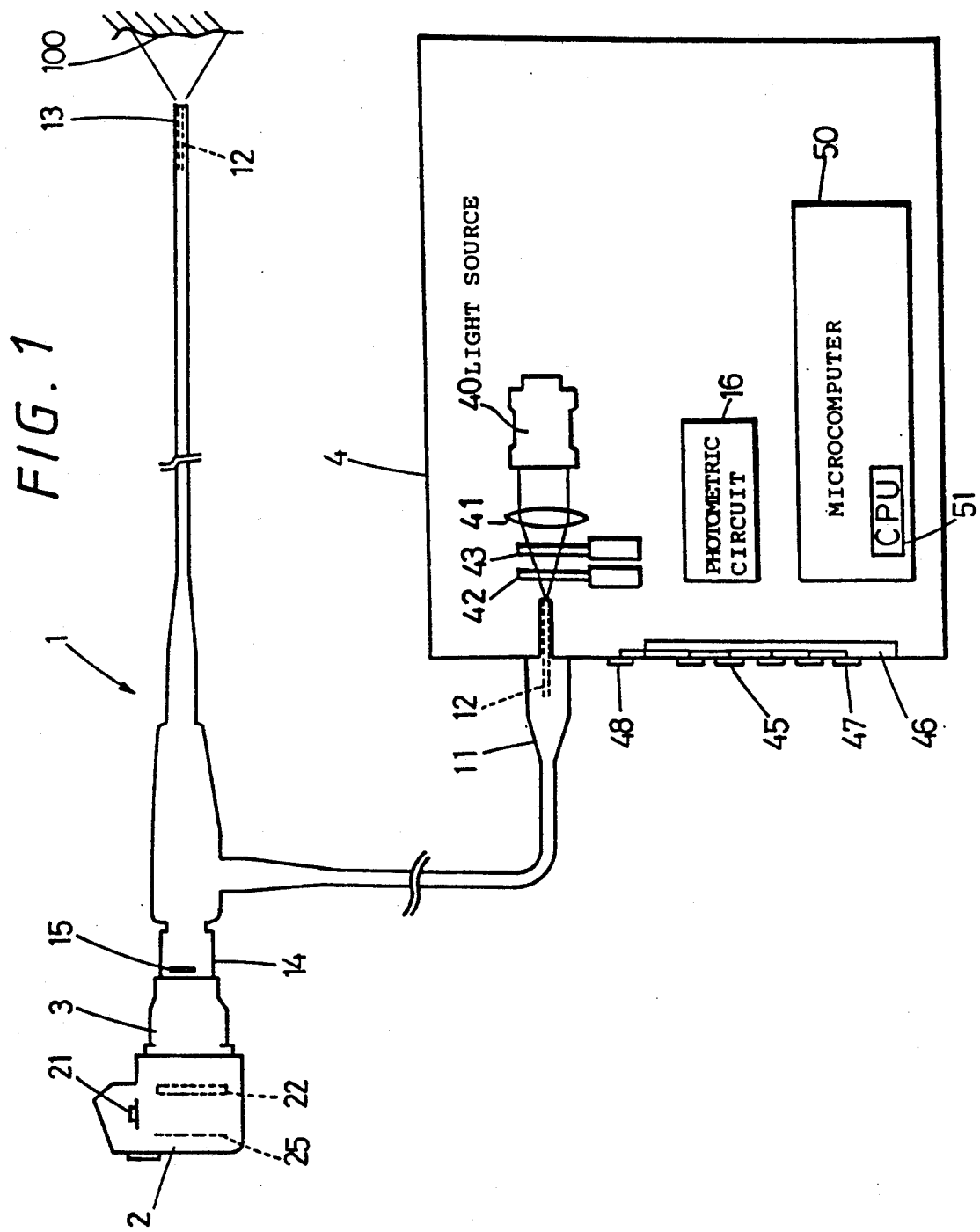
FIG. 1 schematically shows the whole arrangement of a photographing system of an endoscope.

FIG. 1 shows a photographing system of an endoscope. Reference numeral 1 denotes an endoscope. A camera (photographing device) 2 is detachably attached to an eyepiece 14 of the endoscope 1 through an adapter 3.

Reference numeral 4 denotes a light source apparatus, to which is detachably connected a connector 11 of the endoscope 1. Illuminating light that is emitted from a light source (lamp) 40 is condensed through a condenser lens 41 and supplied to an illuminating light guide fiber bundle 12 in the endoscope 1.

In an illuminating light path which extends between the light source 40 and the light guide fiber bundle 12 is provided a shutter (light source shutter) 42, which can be opened and closed to fully open and close the illuminating light path. A diaphragm 43 is also provided in the illuminating light path, which is capable of varying the area of passage of the illuminating light.

The illuminating light is transmitted through the light guide fiber bundle 12 and applied to an object 100 from the distal end 13 of an insert part of the endoscope 1. The reflected light from the object 100 is transmitted through an image guide fiber bundle (not shown) to expose the plane (photographic plane) of a film 25 in the camera 2. A shutter (camera shutter) 22 in the camera 2 is opened for a predetermined time (e.g., 0.25 sec) only when a synchro switch 21 is turned on.

A light-receiving element 15 is provided in the eyepiece 14 to convert a Brightness level of the exposure light that is applied to the plane of the film 25 into an electric signal. the output voltage from the light-receiving element 15 is integrated in a photometric (integration) circuit 16, and an integral state value is output from the photometric circuit 16. Reference numeral 45 denotes a data input switch which is provided on an operation panel 46 that is attached to the surface of the light source apparatus 4 to input various kinds of data for setting an exposure index.

Examples of data for setting an exposure index include the type of endoscope, the type of photographing device, the sensitivity of a film, the magnification of an adapter, and exposure compensation data.

A brightness setting switch 47 is used to input a bright level of illuminating light during observation. A light source switch 48 is used to turn on the light source 40. A microcomputer 50 incorporates a central processing unit (CPU) 51.

Figure 2:
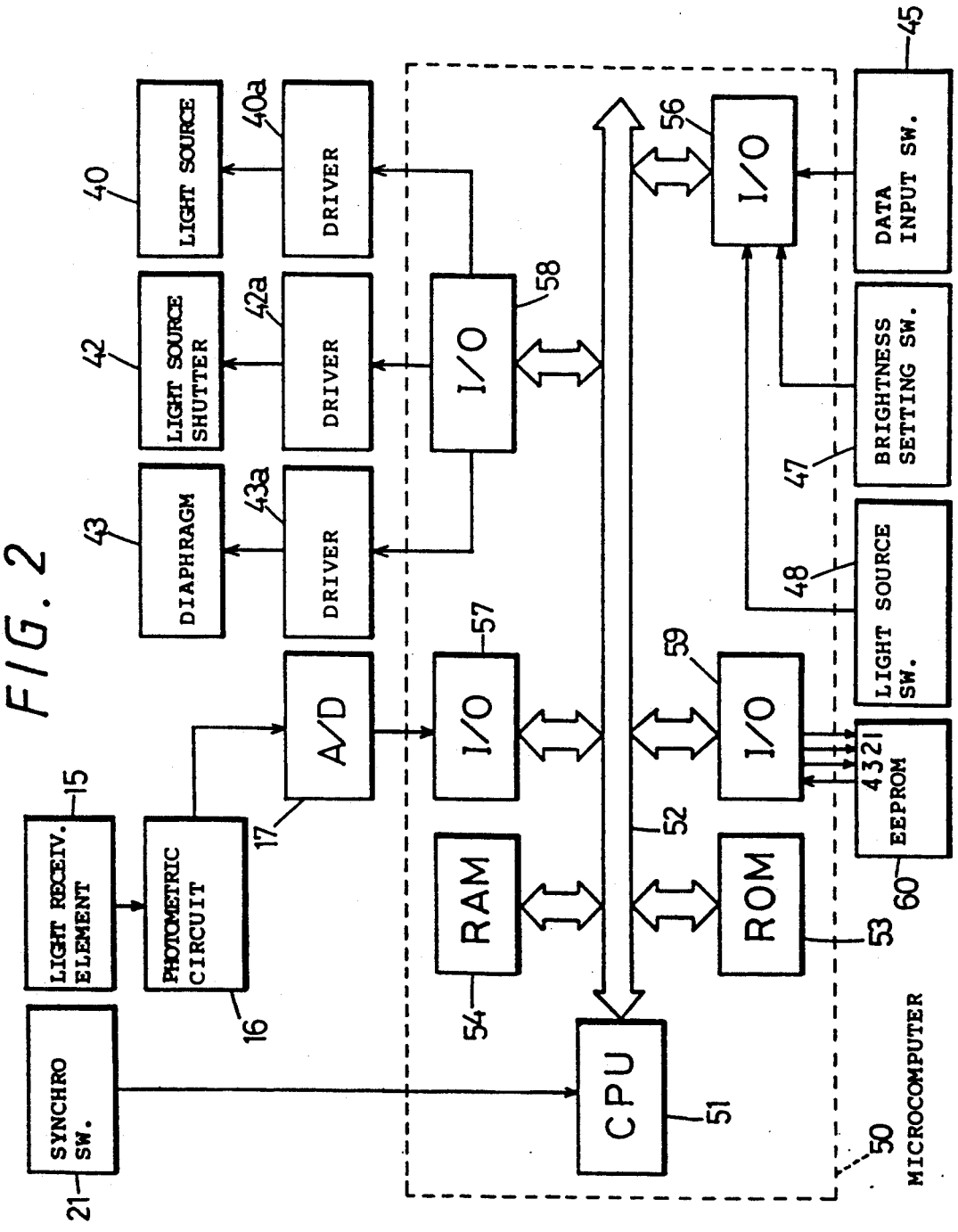
FIG. 2 is a circuit block diagram of one embodiment of the present invention.

Referring to FIG. 2, which is a block diagram showing the electrical arrangement of this embodiment, the microcomputer 50 includes a read only memory (ROM) 53 and a random access memory (RAM) 54, which are connected to the CPU 51 through a system bus 52. The RAM 54 is employed as a stack area, for example, for the storage of data. The CPU 51 is supplied with an interrupt signal which is outputted from the synchro switch 21.

The system bus 52 is further connected with first to fourth input/output ports 56, 57, 58 and 59.

The data input switch 45, the brightness setting switch 47 and the light source switch 48 are connected to the input terminal of the first input/output port 56.

The output from the light-receiving element 15 is integrated in the photometric (integration) circuit 16 to obtain an integral state value (integral output voltage V), which is input to the input terminal of the second input/output port 57 through an analog-to-digital converter 17.

The output terminal of the third input/output port 58 is connected to drivers 40a, 42a and 43a which respectively control the brightness of light that is emitted from the light source 40, the opening and closing operation of the light source shutter 42, and the degree of opening of the diaphragm 43.

The fourth input/output port 59 is connected with an electrically erasable programmable read only memory (EEPROM) in which stored data can be erased and programmed. The EEPROM 60 is stored, for example, with combinations of data which are frequently input through the data input switch 45, or data representative of exposure conditions that are calculated on the basis of the combinations of data.

The EEPROM 60 has three mode control input terminals, that is, a chip select terminal, a shift clock terminal and an input terminal and one output terminal. A particular operation timing is set for each mode control input terminal, so that, even if a noise is generated in the system bus 52, no data in the EEPROM 60 will be erased or rewritten accidentally.

Although in this embodiment the EEPROM 60 has a plurality of mode control input terminals which are provided in parallel, the arrangement may also be such that instruction codes and operating timings are individually set for reading, writing and erasing and these signals are input using a single mode control input terminal.

In actual use, when a memory set switch (not shown), that is provided in the data input switch 45, is depressed, data that is input at present is stored into the EEPROM 60, whereas, when another memory switch (not shown) that is provided in the data input switch 45 is depressed, the data stored in the EEPROM 60 is read out and a set voltage $V_r$ is then calculated on the basis of the readout data.

During a photographing operation, automatic exposure time control is effected on the basis of the set voltage $V_r$ calculated as described above.

Figure 3:
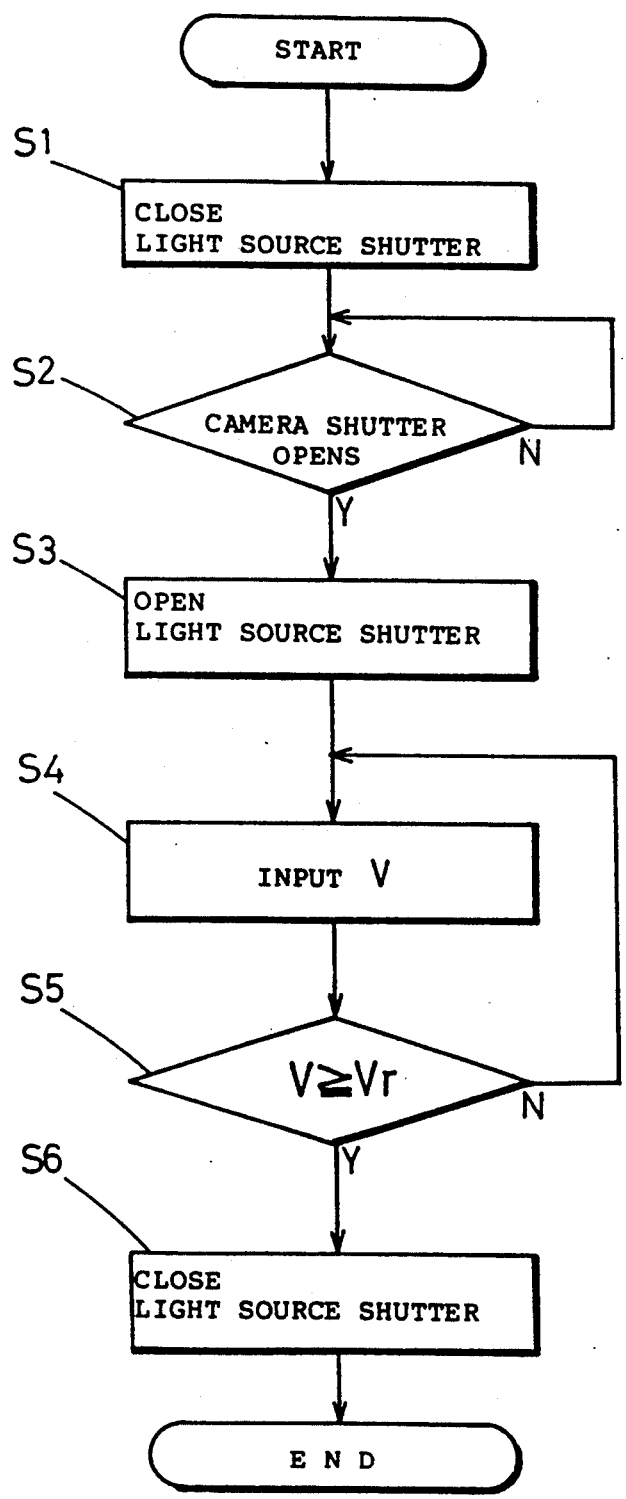
FIG. 3 is a flowchart showing a simple exposure control process.

FIG. 3 is a flowchart showing the simplest control process that is executed in the microcomputer 50 to effect automatic exposure time control. In the figure, S denotes Steps.

This process is started, for example, by turning on the synchro switch 21 on the camera 2. The light source shutter 42 is closed in S1, and when the camera shutter 22 opens in S2, the light source shutter 42 is opened in S3. Then, the integral output voltage V is input from the photometric circuit 16 in S4.

If the integral output voltage V is lower than the set voltage $V_r$ in S5, the process returns to S4 to repeat the sequence from the input of the integral output voltage V, whereas, if the integral output voltage V reaches the set voltage $V_r$, the light source shutter 42 is closed in S6, thus completing the operation.

Figure 4:
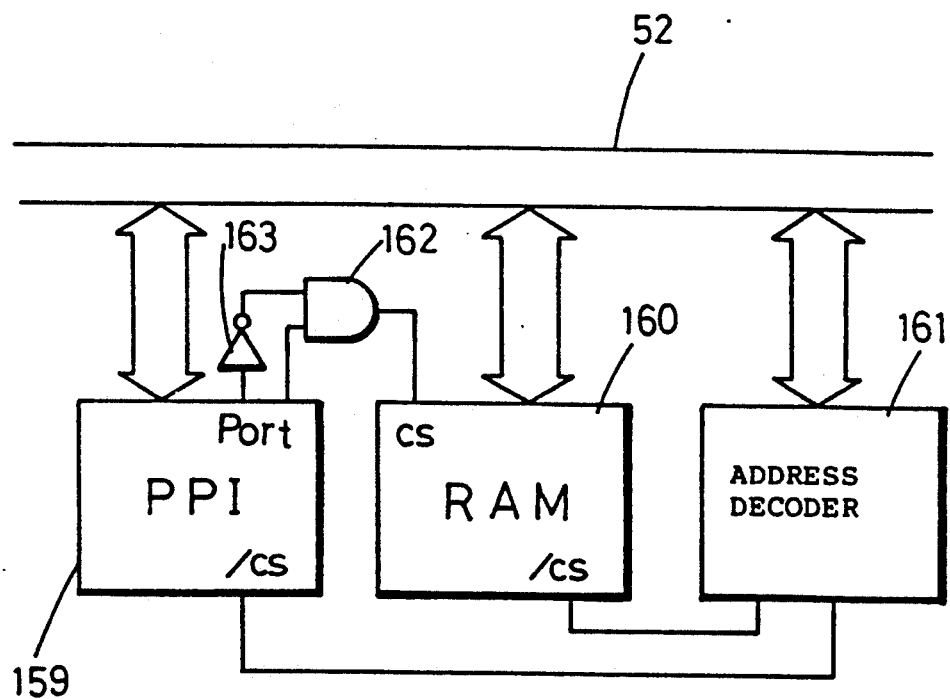
FIG. 4 is a block diagram showing a part of the circuit of a second embodiment of the present invention.

FIG. 4 shows a second embodiment of the present invention, in which a combination of a random access memory (RAM) 160, a programmable input/output interface (PPI) 159 and an address decoder 161 is employed in place of the combination of the EEPROM 60 and the input/output port 59 in the first embodiment, and in which chip select terminals (CS and /CS terminals) of the RAM 160 and PPI 159 are activated by the address decoder 161 or the PPI 159, thereby selecting the RAM 160 through the PPI 159.

It should be noted that the term "chip select terminal" means one or two input terminals that are provided on one or a plurality of devices, e.g., memories and input/output devices, which are connected to a system bus of a CPU51, to enable the desired device.

The RAM 160 is provided with the two chip select terminals, that is, a /CS terminal that is activated in response to a low-level signal input from the address decoder 161, and a CS terminal that is activated in response to a high-level signal input from the PPI 159. Therefore, the RAM 160 is enabled when both of the chip select terminals are activated.

The PPI 159 is provided with a chip select terminal, that is, a /CS terminal that is activated in response to a low-level signal input from the address decoder 161. The PPI 159 is enabled when the chip select terminal /CS is activated.

The address decoder 161 receives an address signal that is sent from the CPU 51 through the system bus 52, and generates and outputs a low-level signal for activating the chip select terminals /CS of the RAM 160 and /CS of the PPI 159 only when the RAM 160 is to be accessed.

One output port of the PPI 159 is connected directly to one input terminal of an AND circuit 162, and another output port is connected to the other input terminal of the AND circuit 162 through an inverter 163. The output terminal of the AND circuit 162 is connected to the CS terminal of the RAM 60. The CS terminal of the RAM 160 is held at the low level at all times during a normal operation so that the RAM 160 is not selected, and only when the RAM 160 is to be accessed, the CS terminal of the RAM 160 is raised to the high level through the ports of the PPI 159 and the AND circuit 162 to enable the RAM 160, according to a signal from the CPU through the system bus 52.

Accordingly, when data is to be actually read out from or written into the RAM 160, the ports of the PPI 159 are controlled so that the CS terminal of the RAM 160 is set to the high level.

Upon completion of the reading or writing of data, the CS terminal of the RAM 160 is set to the low level through the ports of the PPI 159.

By virtue of the above-described arrangement, even if all the terminal ports of the PPI 159 are undesirably set to either the high or low levels by the generation of a large noise, the RAM 160 is not selected and there is therefore no possibility that the data stored therein will be erased or rewritten.

Although in the foregoing embodiments the stored data are those which are used to set an exposure index for automatic exposure photographing, it should be noted that the present invention is not necessarily limited thereto and that the stored data may be any kind of data, for example, those which are used to control the brightness of illuminating light that is supplied to the endoscope during observation, or those which are used for setting letters which are to be superimposed on a picture taken through the endoscope.

According to the present invention, there is no fear that data stored in a programmable memory will be destroyed by a noise or other disturbance, so that the reliability of data is enhanced and it is possible to eliminate the occurrence of a maloperation caused by the stored data.

While the invention has been described by reference to specific embodiments chosen for purposes of illustration, it should be apparent that numerous modifications could be made thereto by those skilled in the art without departing from the basic concept and scope of the invention.

We claim:

1. A light source aparatus for an endoscope comprising:
   a light source for supplying light to said endoscope for illuminating an object;
   a microcomputer for effecting operation control; and
   an erasable programmable read only memory for storing data that is used in said microcomputer, wherein said erasable programmable read only memory has a plurality of mode control input terminals at which different respective operating timings are set, and said data comprises values to set exposure conditions for taking one or more photographs.

2. A light souce apparatus for an endoscope according to claim 1, wherin said erasable programmable read only memory is an electricaly erasable programmable read only memory.

3. A light source apparatus for an endoscope according to claim 1, wherein said data is used to set an exposure index for effecting automatic exposure control in said microcomputer.

4. A light source apparatus for an endoscope comprising:
   a light source for supplying light to said endoscope for illuminating an object;
   a microcomputer for effecting operation control;
   an erasable programmable read only memory for storing data that is used in said microcomputer, whrein said data comprises values to set exposure conditions for taking one or more photographs; and
   a system bus which ocnnects siad microcompute with sid erasable progrtammable read only memory, wherin said erasable programmable read only memory is isolated from said system bus to protect said erasable programmable read only memory from system noise.

5. A light source apparatus for an endoscope comprising:
   a light source for supplying light to said endoscope for illuminating an object;
   am icrocomputer for effecting operation control; and
   an erasable programmable read only memory for storing data that is used in said microcomputer, whrein said erasable programmable read only memory has a single mode control input terminal at which instruction codes and operation timings are individually set for reading, writing and erasing, and wherein said data comprises values to set exposure conditions for taking one or more photographs.

6. A lgith source appratus for an endoscope comprising:
   a light source for supplying light to said endoscope for illuminating an object;
   a microcomputer for effecting operation control; and
   a random access memory fort storing data that is used in said microcomputer, said random access memory having a chip select terminal connected to a programmable input/output interface, which is connected to a system bus of said microcomputer, in such a manner that said random access memory will not be selected when all output ports of said interface are set to either a high or low level.

7. A lgiht source apparatus for an endoscope according to claim 6, wherein said data is used to set an exposure index for effecting automatic exposure control in said microcomputer.

8. A light source apparatus for an endoscope according to claim 6, wherein one output port of said programmable input/output interface that is connected to said system bus is conncected directly to a first input terminal of an AND circuit, another output port of said interface is connected to a second input terminal of said AND circuit through an invertor, and the output terminal of said AND circuit is connected to said chip select terminal of said random access memory.

9. A light source apparatus for an endoscope according to claim 8, wherein said chip select terminal of said random access memory is activated to enable siad random access memory through said programmable input/output interface and said AND circuit only when said random acces memory is accessed.

10. A light source apparatus for an endoscope comprising:
    a light source for supplying light to said endoscope;
    a microcomputer for effecting operation control;
    a random acces memory for storing data that is used in said microcomputer; and
    means for disabling said random access memory when external noise occurs, which is responsive to external noises to protect said random access memory from data destruction, wherein said means for disabling comprises a programmable input/output interface.

11. A light source apparatus for an endoscope comprising:
    a light source for supplying light to said endoscope for illuminating an object;
    a microcomputer for effecting operation control;
    an erasable programmable read only memory for storing data that is used in said microcomputer, wherein said data comprises values to set exposure conditions for taking one or more photographs;
    means for isolating said erasable programmable read only memory from said light source to protect said erasable programmable read only memory from noise, wherein said means for isolating further isolates said erasable programmable read only memory from said microcomputer to protect said erasable programmable read only memory from noise.

12. A light source apparatus for an endoscope as in claim 11, wherein said means for isolating comprises an input/output port.

* * * * *

UNITED STATES PATENT AND TRADEMARK OFFICE
CERTIFICATE OF CORRECTION

PATENT NO. : 5,220,912

DATED : June 22, 1993

INVENTOR(S) : M. NAKASIMA et al.

It is certified that error appears in the above-indentified patent and that said Letters Patent is hereby corrected as shown below:

At column 5, line 26 (claim 2, line 2), change "wherin" to ---wherein---.

At column 5, line 27 (claim 2, line 3), change "electricaly" to ---electrically---.

At column 5, line 41 (claim 4, line 8), change "whrein" to ---wherein---.

At column 5, line 44 (claim 4, line 11), change "ocnnects" to ---connects---.

At column 5, line 44 (claim 4, line 11), change "siad" to ---said---.

At column 5, line 44 (claim 4, line 11), change "microcompute" to ---microcomputer---.

At column 5, line 45 (claim 4, line 12), change "sid" to ---said---.

At column 5, line 45 (claim 4, line 12), change "progartammable" to ---programmable---.

At column 5, line 46 (claim 4, line 13), change "wherin" to ---wherein---.

At column 5, line 54 (claim 5, line 5), change "am icrocomputer" to ---a microcomputer---.

At column 5, line 57 (claim 5, line 8), change "whrein" to ---wherein---.

At column 6, line 1 (claim 6, line 1), change "laith" to ---light---.

UNITED STATES PATENT AND TRADEMARK OFFICE
CERTIFICATE OF CORRECTION

PATENT NO. : 5,220,912
DATED : June 22, 1993
INVENTOR(S) : M. NAKASIMA et al.

It is certified that error appears in the above-indentified patent and that said Letters Patent is hereby corrected as shown below:

At column 6, line 29 (claim 9, line 3), change "siad" to ---said---.

Signed and Sealed this

Twenty-third Day of August, 1994

Attest:

BRUCE LEHMAN

Attesting Officer

Commissioner of Patents and Trademarks